US00PP24426P2

(12) United States Plant Patent
Li

(10) Patent No.: US PP24,426 P2
(45) Date of Patent: May 6, 2014

(54) ***VERBENA* PLANT NAMED 'KLEVP12446'**

(50) Latin Name: *Verbena×hybrida*
Varietal Denomination: KLEVP12446

(71) Applicant: Klemm+Sohn GmbH & Co. KG, Stuttgart (DE)

(72) Inventor: Ruijun Li, North Parramata (AU)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 30 days.

(21) Appl. No.: 13/573,957

(22) Filed: Oct. 16, 2012

(51) Int. Cl.
*A01H 5/00* (2006.01)

(52) U.S. Cl.
USPC ..... Plt./308

(58) Field of Classification Search
USPC ..... Plt./308
See application file for complete search history.

*Primary Examiner* — Kent L Bell
(74) *Attorney, Agent, or Firm* — Jondle Plant Sciences Division of Swanson & Bratschun, L.L.C.

(57) ABSTRACT

A new and distinct variety of *Verbena* plant named 'KLEVP12446', particularly characterized by having dark red flower color, a freely branching growth habit, and resistance to powdery mildew, is disclosed.

1 Drawing Sheet

Genus and species: *Verbena×hybrida.*
Variety denomination: 'KLEVP12446'.

BACKGROUND OF THE NEW PLANT

The present invention comprises a new and distinct variety of *Verbena*, botanically known as *Verbena×hybrida*, and hereinafter referred to by the variety name 'KLEVP12446'. The new variety is the result of a cross conducted in July 2008 in Cobbity, New South Wales, Australia between female parent *Verbena* plant, 'F 2' (unpatented), and male parent *Verbena* plant, 'V842' (unpatented). A single plant selection was subsequently chosen for further evaluation and asexual propagation.

The new variety was first propagated in October 2008 in Cobbity, New South Wales, Australia by vegetative cuttings and has been asexually reproduced repeatedly by vegetative cuttings for three to four generations. 'KLEVP12446' has been found to retain its distinctive characteristics through successive asexual propagations.

Plant Breeder's Rights for this variety were applied for in Canada on Feb. 6, 2012. 'KLEVP12446' has not been made publicly available anywhere in the world more than one year prior to filing of this application.

SUMMARY OF THE INVENTION

The following are the most outstanding and distinguishing characteristics of this new variety when grown under normal horticultural practices in a greenhouse in Sydney, Australia.

1. Dark red flower color;
2. Freely branching growth habit; and
3. Resistance to powdery mildew.

DESCRIPTION OF THE PHOTOGRAPH

This new *Verbena* plant is illustrated by the accompanying photograph which shows the foliage and inflorescence of the plant. The colors shown are as true as can be reasonably obtained by conventional photographic procedures. The photograph is of a plant about 3 months old, taken in the spring of 2011, grown from a rooted cutting in a glass greenhouse in Stuttgart, Germany under normal horticultural practices.

DESCRIPTION OF THE NEW VARIETY

The following detailed descriptions set forth the distinctive characteristics of 'KLEVP12446'. The data which define these characteristics were collected from asexual reproductions carried out in Stuttgart, Germany. The plant history was taken in June 2011 on 3-month old plants grown in 12 centimeter pots in a glass greenhouse with a pinch date at week 10. The color readings were determined under natural light. Color references are to The R.H.S. Colour Chart of The Royal Horticultural Society of London (R.H.S.), Fifth Edition (2007).

DESCRIPTION OF THE NEW PLANT

Classification:
- *Family.*—Verbenaceae.
- *Genus and species.*—*Verbena×hybrida.*
- *Common name.*—*Verbena.*
- *Denomination.*—'KLEVP12446'.

Parentage:
- *Female parent.*—*Verbena* plant, 'F 2' (unpatented).
- *Male parent.*—*Verbena* plant, 'V842' (unpatented).

Plant:
- *Form.*—Semi-trailing.
- *Growth and branching habit.*—Freely branching.
- *Height (from top of soil).*—Approximately 20.0 cm.
- *Width (horizontal plant diameter).*—Approximately 40.0 cm.
- *Time to produce a finished flowering plant.*—Approximately 8 weeks.
- *Time to initiate and develop roots.*—3 weeks.
- *Root description.*—Fine; RHS 155B.

Stems:
- *Number of branches per plant.*—Greater than 20.
- *Length.*—Approximately 20.0 cm.

*Diameter per branch* (*measured from the midpoint*).—2.0 mm.
*Internode length.*—3.0 cm.
*Color.*—RHS 139C.
*Anthocyanin.*—Absent.
*Texture and appearance.*—Sparse pubescence.

Leaves:
*Arrangement.*—Opposite.
*Color.*—Upper surface (both immature and mature leaves): RHS 139C. Lower surface (both immature and mature leaves): RHS 139D.
*Length.*—2.5 cm.
*Width.*—1.5 cm.
*Shape.*—Elliptic.
*Apex.*—Cuspidate.
*Base.*—Closed.
*Margin.*—Serrated.
*Texture* (*both upper and lower surfaces*).—Leathery.
*Venation pattern.*—Palmate.
*Venation color.*—RHS 139C.
*Petioles.*—Length: 0.5 cm. Diameter: Less than 0.2 cm. Color: RHS 139C. Texture: Rough.

Flower buds:
*Shape.*—Tall cylinder.
*Length.*—0.5 cm.
*Diameter.*—Less than 0.1 cm.
*Color* (*at tight bud*).—RHS 139C.

Inflorescence:
*Blooming habit* (*flowering season*).—From early spring to late fall in central Europe.
*Lastingness of individual blooms on the plant.*—2 weeks.
*Fragrance.*—Absent.
*Inflorescence type.*—Umbel.
*Length of inflorescence.*—3.0 cm.
*Diameter of inflorescence.*—6.0 cm.
*Number of florets per inflorescence.*—Approximately 20.
*Peduncle.*—Length: 3.0 cm. Diameter: 0.1 cm. Color: RHS 139C. Texture: Rough.

Florets:
*Form.*—Tall cylinder, opening at the end.
*Length.*—0.4 cm.
*Diameter.*—Less than 0.1 cm.
*Color.*—Immature flower: Upper surface: RHS 139C. Lower surface: RHS 141D. Mature flower: Upper surface: RHS 44B. Lower surface: RHS 44C.
*Corolla tube length.*—2.0 cm.
*Corolla tube color.*—RHS 139C.
*Petals.*—Length of lobe: 0.5 cm. Diameter of lobe: 0.4 cm. Lobe shape: Reniform. Apex: Obtuse. Base: Closed. Margin: Entire.
*Pedicels.*—Not visible.

Calyx:
*Arrangement.*—Round.
*Sepals.*—Shape: Funnel. Length: 2.0 cm. Diameter: Less than 0.1 cm. Color: RHS 139C. Apex: Wide open. Base: Open. Texture: Smooth, margin satiny.

Reproductive organs:
*Stamens.*—Quantity: Greater than 5. Shape: Lanceolate. Color: RHS 139D. Filament length: Less than 0.1 cm. Filament diameter: Less than 0.1 cm.
*Anther.*—Shape: Fused. Color: RHS 139D. Length: Less than 0.1 cm. Diameter: Less than 0.1 cm. Pollen: Quantity: None observed. Pistils: Quantity: 1. Length: 0.2 cm. Diameter: Less than 0.1 cm. Stigma: Color: RHS 139D. Shape: Lanceolate. Length: Less than 0.1 cm. Diameter: Less than 0.1 cm. Style: Color: RHS 139D. Length: Less than 0.1 cm. Diameter: Less than 0.1 cm. Shape: Lanceolate.

Fruit and seed set: None observed.

Disease, insect resistance, and physiological stress: Resistant to powdery mildew.

COMPARISON WITH PARENTAL AND COMMERCIAL VARIETIES

'KLEVP12446' differs from the female parent verbena plant 'F 2' (unpatented), in that 'KLEVP12446' has earlier flowering and better center branching than 'F 2'.

'KLEVP12446' differs from the male parent verbena plant 'V842', in that 'KLEVP12446' has a darker red flower color and larger flower size than 'V842'.

'KLEVP12446' differs from the commercial variety, 'Duempdared' (U.S. Plant Pat. No. 20,152), in that 'KLEVP12446' has better center branching, better leaf quality, larger flowers and earlier flowering time than 'Duempdared'.

I claim:

1. A new and distinct variety of *Verbena* plant named 'KLEVP12446' as shown and described herein.

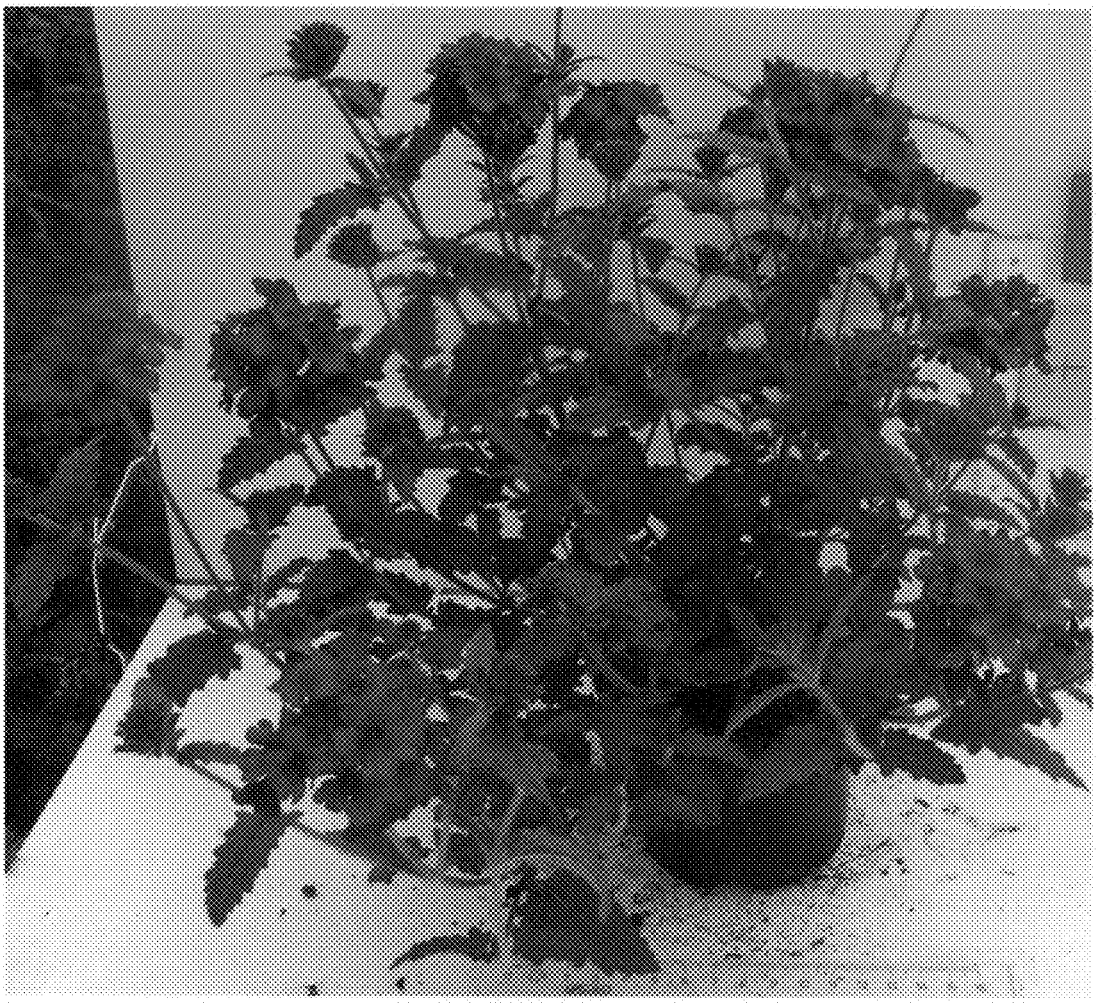

* * * * *